United States Patent
Kawase et al.

(10) Patent No.: US 9,968,308 B2
(45) Date of Patent: May 15, 2018

(54) COMPUTED TOMOGRAPHIC MAMMOGRAPHY APPARATUS AND COMPUTED TOMOGRAPHIC APPARATUS FOR BREAST

(71) Applicant: CANON KABUSHIKI KAISHA, Tokyo (JP)

(72) Inventors: Junya Kawase, Yokohama (JP); Takeo Tsukamoto, Kawasaki (JP); Nobuhiro Ito, Yamato (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days. days.

(21) Appl. No.: 15/023,639

(22) PCT Filed: Nov. 11, 2014

(86) PCT No.: PCT/JP2014/005648
§ 371 (c)(1),
(2) Date: Mar. 21, 2016

(87) PCT Pub. No.: WO2015/075897
PCT Pub. Date: May 28, 2015

(65) Prior Publication Data
US 2016/0206253 A1 Jul. 21, 2016

(30) Foreign Application Priority Data

Nov. 20, 2013 (JP) .................................. 2013-239624
Nov. 20, 2013 (JP) .................................. 2013-239625

(51) Int. Cl.
*A61B 6/03* (2006.01)
*A61B 6/10* (2006.01)
(Continued)

(52) U.S. Cl.
CPC .............. *A61B 6/035* (2013.01); *A61B 6/032* (2013.01); *A61B 6/06* (2013.01); *A61B 6/107* (2013.01); *A61B 6/4435* (2013.01); *A61B 6/502* (2013.01)

(58) Field of Classification Search
None
See application file for complete search history.

(56) References Cited

U.S. PATENT DOCUMENTS 6,164,820 A 12/2000 Hell
6,175,117 B1 1/2001 Komardin
(Continued)

FOREIGN PATENT DOCUMENTS

EP 2407109 A1 1/2012
EP 2586375 A1 5/2013
(Continued)

OTHER PUBLICATIONS

U.S. Appl. No. 15/023,643, filed Mar. 21, 2016.

*Primary Examiner* — Hoon Song
(74) *Attorney, Agent, or Firm* — Canon U.S.A., Inc. IP Division

(57) ABSTRACT

A mammographic CT apparatus includes: a gantry, including a front face plate in which an insertion opening is formed for inserting a breast into an accommodation portion a radiation tube and sensing device disposed within the gantry; a driving unit configured to rotate the radiation tube and the sensing device around a rotation axis set in the normal direction of the accommodation portion, at the same angular speed and in the same direction; a collimator disposed between the accommodation portion and the radiation tube, and configured to rotate around the rotation axis integrally with the radiation tube and sensing device; and an annular shield disposed between the rotational path of the collimator and the rotational path of the radiation tube, having an (Continued)

annular gap corresponding to the rotational path of the collimator, wherein an edge of the collimator or sensing device is fit into the gap.

22 Claims, 15 Drawing Sheets

(51) Int. Cl.
*A61B 6/00* (2006.01)
*A61B 6/06* (2006.01)

(56) References Cited

U.S. PATENT DOCUMENTS

| | | | |
|---|---|---|---|
| 6,987,831 | B2 | 1/2006 | Ning |
| 2004/0234021 | A1 | 11/2004 | Hoffman |
| 2006/0262898 | A1 | 11/2006 | Partain |
| 2007/0098141 | A1 | 5/2007 | Hjarn |
| 2008/0049904 | A1* | 2/2008 | Beyerlein ............ A61B 6/107 378/197 |
| 2009/0080604 | A1 | 3/2009 | Shores |
| 2011/0096897 | A1 | 4/2011 | Tonami |
| 2014/0093035 | A1* | 4/2014 | Beekman ............... A61B 6/06 378/37 |
| 2014/0119505 | A1* | 5/2014 | Ohi ...................... A61B 6/037 378/37 |

FOREIGN PATENT DOCUMENTS

| | | |
|---|---|---|
| JP | 2004105729 A | 4/2004 |
| JP | 2008093135 A | 4/2008 |
| JP | 2010075338 A | 4/2010 |
| JP | 2012120651 A | 6/2012 |
| JP | 2013-22040 A | 2/2013 |
| JP | 2013-22041 A | 2/2013 |
| WO | 2008/054279 A1 | 5/2008 |

* cited by examiner

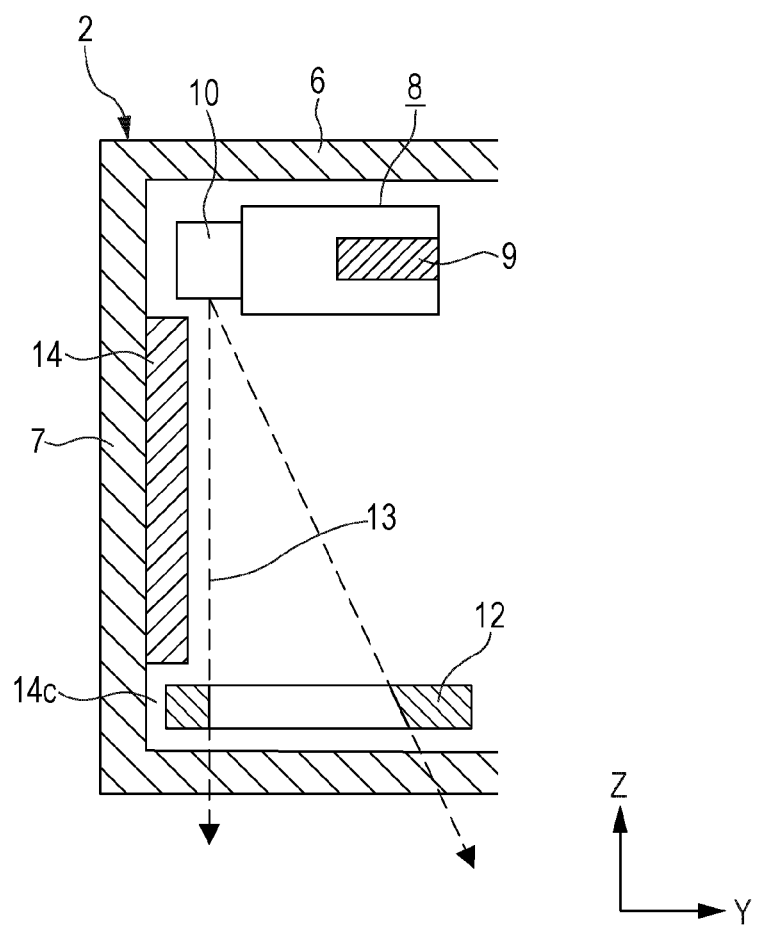

COMPUTED TOMOGRAPHIC MAMMOGRAPHY APPARATUS AND COMPUTED TOMOGRAPHIC APPARATUS FOR BREAST

TECHNICAL FIELD

The present invention relates to a medical computed tomography (hereinafter, "CT") apparatus, and more particularly relates to a computed tomographic mammography apparatus (hereinafter, "mammographic CT apparatus" used for taking images of breasts.

BACKGROUND ART

In addition to breast cancer examinations by palpation and ultrasound diagnosis, mammographic CT apparatuses have come to be used which can display within the breast in three-dimensional (3D) images.

PTL 1 discloses CT breast imaging made up of a gantry to which a cone-beam radiation source and a sensing device are mounted. The subject lies prone on a table having a breast insertion opening, with the gantry located so as to surround the breast.

CITATION LIST

Patent Literature

PTL 1: U.S. Pat. No. 6,987,831

SUMMARY OF INVENTION

Technical Problem

In a conventional mammographic CT apparatus, the breast is inserted from the insertion opening into an accommodation portion, while the breastbone is pressed against the upper face of a top panel. The breast overlaps an X-ray irradiation area in the accommodation portion which is irradiated by the X-rays, the X-rays which have transmitted through the breast are sensed by the sensing device, and thus an X-ray transmission image of the breast can be taken. The X-ray irradiation region of the mammographic CT apparatus needs to be close to the top panel, so that images of the portions of the breast near the breastbone (the portions around the base of the breast) can also be taken. The sensing device also is preferably located as close as possible to the top panel.

On the other hand, leakage of X-rays to the subject side must be prevented. The apparatus according to PTL 1 has a configuration where a collimator defining the X-ray irradiation region is integrally built into the X-ray generator, around the focal point. However, the collimator built into the X-ray generator is at a position away from the sensing device, so an X-ray penumbra is formed at a wide region on the outer side of the X-ray irradiation region. Accordingly, the collimator alone placed near the focal point cannot sufficiently prevent leakage of X-rays to the subject.

Providing the collimator at a position near the sensing device enables occurrence of the penumbra to be suppressed. Also, the collimator is preferably situated near the top panel so as to being the X-ray irradiation region close to the top panel. However, an X-ray shield disposed on the inner side of the top panel to prevent leakage of X-rays interferes with the collimator, so the collimator cannot be brought into proximity with the top panel beyond a certain extent.

On the other hand, the sensing device has a sensing area around the middle thereof where sensing of X-rays is performed by a sensing element, and a non-sensing area on the perimeter where wiring circuits and the like are laid out, and X-rays cannot be sensed. In order to enable images to be taken up to the base portion of the breast, the sensing area needs to be brought into proximity with the top panel, but this is restricted by the existence of the non-sensing area. Also, the X-ray shield disposed on the inner side of the top panel interferes with the sensing device, so the sensing device cannot be brought into proximity with the top panel beyond a certain extent.

The present invention provides a mammographic CT apparatus using radiation such as X-rays, in which both prevention of leakage of radiation to the subject side, and radiographs to the base of the breast, are realized.

Solution to Problem

A mammographic CT apparatus according to the present invention includes:

a gantry, including a front face plate in which an insertion opening is formed for inserting a breast into an accommodation portion;

a radiation tube disposed within the gantry;

a sensing device disposed within the gantry so as to face the radiation tube, and configured to sense radiation which has been emitted from the radiation tube and been transmitted through the accommodation portion;

a driving unit configured to rotate the radiation tube and the sensing device around a rotation axis set in the normal direction of the accommodation portion, at the same angular speed and in the same direction;

a collimator disposed between the accommodation portion and the radiation tube, and configured to rotate around the rotation axis integrally with the radiation tube and sensing device; and an annular shield disposed between the rotational path of the collimator and the rotational path of the radiation tube, having an annular gap corresponding to the rotational path of the collimator, wherein an edge of the collimator is fit into the gap.

Further, a mammographic CT apparatus according to the present invention includes:

a gantry, including a front face plate in which an insertion opening is formed for inserting a breast into an accommodation portion;

a radiation tube disposed within the gantry;

a sensing device disposed within the gantry so as to face the radiation tube, and configured to sense radiation which has been emitted from the radiation tube and been transmitted through the accommodation portion;

a driving unit configured to rotate the radiation tube and the sensing device around a rotation axis set in the normal direction of the accommodation portion, at the same angular speed and in the same direction; and an annular shield which surrounds the perimeter of the insertion opening, disposed on an inner side of the front face plate, and having an annular gap corresponding to the rotational path of the sensing device, wherein an edge of the sensing device is fit into the gap.

Further features of the present invention will become apparent from the following description of exemplary embodiments with reference to the attached drawings.

BRIEF DESCRIPTION OF DRAWINGS

FIG. 3 is an enlarged view of around a collimator according to the first embodiment.

DESCRIPTION OF EMBODIMENTS

Figure 1:
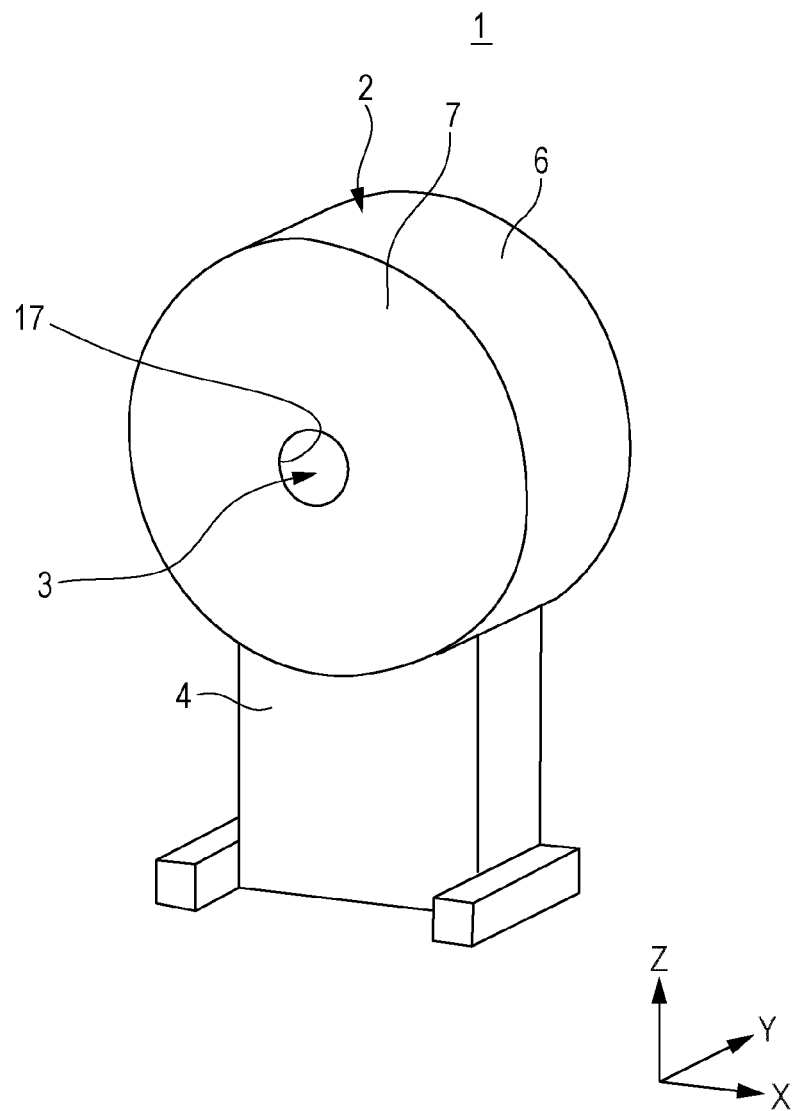
FIG. 1 is an overall perspective view of a mammographic CT apparatus according to the present invention.

Embodiments to carry out the present invention will be described with reference to the drawings. Note that in the drawings referenced below, the same reference numerals denote the same components.

First Embodiment

Overview of Mammographic CT Apparatus

A mammographic CT apparatus 1 includes a gantry 2 configuring a chamber within which is stored a radiation tube 8, a collimator 12, and so forth, as illustrated in FIGS. 1 through 3. At the center portion of the gantry 2 is provided an accommodation portion 3 into which a breast 15 of a subject P is inserted. A supporting portion 4 supports the gantry 2.

The gantry 2 is a hollow disc-shaped member, having an inner peripheral plate 5 which surrounds the accommodation portion 3, an outer peripheral plate 6 which surrounds the outer periphery, a front face plate 7 which connects the inner peripheral plate 5 and the outer peripheral plate 6 at the front side, and an unshown back plate which covers the back side. The front face plate 7 has formed therein an insertion opening 17 through which the breast 15 is inserted to and removed from the accommodation portion 3. The radiation tube 8, a sensing device 11, and a later-described collimator 12 are supported by a rotating plate (omitted from illustration) within the gantry 2, so that these three are integrally rotated by a driving unit 101 (see FIG. 4) during CT imaging. This rotation is performed on a rotational axis D established in the normal direction of the insertion opening 17. The rotational axis D passes through the inner side of the accommodation portion 3 and extends in the direction of insertion and removal of the breast 15 to and from the accommodation portion 3 (Y direction). Accordingly, the radiation tube 8, sensing device 11, and collimator 12 are rotated at the same angular speed. When imaging with the mammographic CT apparatus 1, the subject P inserts a breast 15 into the accommodation portion 3 through the insertion opening 17, from the front face side of the front face plate 7 of the gantry 2, and maintains this posture for CT imaging. Note that the front face plate 7 is erect in the present embodiment, so the subject P stands in front of the front face plate 7 for the examination. However, the mammographic CT apparatus 1 according to the present invention may be laid sideways, so that the front face plate 7 serves as the top panel of the above-described related art, with the subject P lying prone on the front face plate 7 for the examination. In this case, the inner peripheral plate 5 may be omitted.

Radiation Tube

Figure 2A:
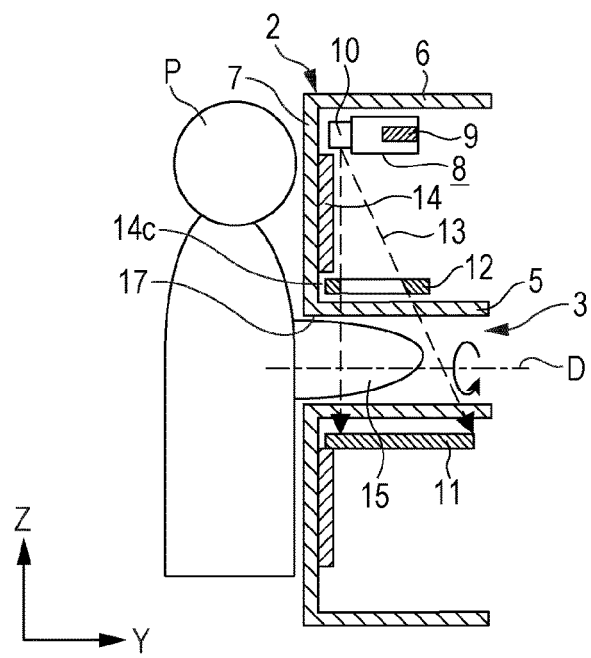
FIG. 2A is a cross-sectional view of a mammographic CT apparatus according to a first embodiment, as viewed from the X direction in FIG. 1.
Figure 2B:
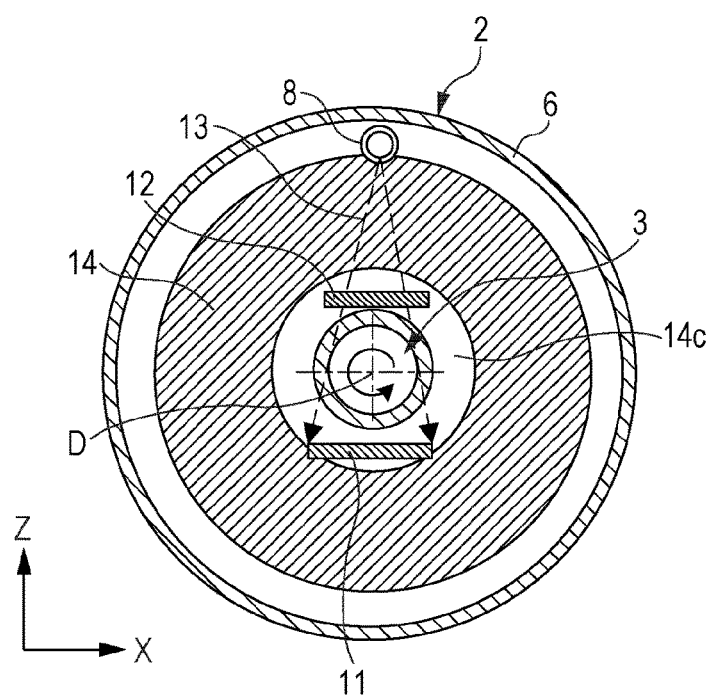
FIG. 2B is a cross-sectional view of the mammographic CT apparatus according to the first embodiment, as viewed from the Y direction in FIG. 1.

As illustrated in FIGS. 2A, 2B, and 3, the radiation tube 8 is a transmissive radiation tube, including an electron gun 9 to generate an electron beam, and an emitter 10. A heat filament type electron source, for example, can be used for the electron gun 9. The emitter 10 has a transmitting target, where a target layer that generates radiation under irradiation of the electron beam from the electron gun 9 is layered on a radiation transmitting support substrate. The material making up the support substrate is preferably one which has sufficient strength to support the target layer, absorbs little radiation generated at the target layer, and has high thermal conductivity, so that heat generated at the target layer can be quickly dissipated. Examples of such a material include diamond, silicon carbide, aluminum nitride, and so forth.

The material making up the target layer preferably has a high melting point and high radiation generation efficiency. Examples of this material include tungsten, tantalum, molybdenum, alloys thereof, and so forth. The radiation tube 8 is supported by an unshown rotating plate which is rotated by the driving unit 101 (see FIG. 4), and rotates on the rotational axis D extending in the direction of insertion and removal of the breast 15 to and from the accommodation portion 3.

Sensing Device

The sensing device 11 is provided at a position facing the radiation tube 8 (emitter 10) across the accommodation portion 3. The sensor area of the sensing device 11 is usually a size which matches an irradiation region 13 of radiation which is defined by the later-described collimator 12. The shape of the sensor area is square, to match the shape of the irradiation region 13. The sensing device 11 is supported by the unshown rotating plate which is rotated by the driving unit 101 (see FIG. 4), along with the radiation tube 8. The sensing device 11 rotates on the rotational axis D extending in the direction of insertion and removal of the breast 15 to and from the accommodation portion 3, in the same direction and the same angular speed as the radiation tube 8, by the rotation of the rotating plate.

Collimator

The collimator 12 is disposed between the radiation tube 8 and accommodation portion 3 at a position near the accommodation portion 3, as illustrated in FIGS. 2A, 2B, and 3, to define the irradiation region 13 of radiation emitted from the radiation tube 8. The collimator 12 is supported by the unshown rotating plate supporting the radiation tube 8 and sensing device 11, and integrally rotates with the radiation tube 8 and sensing device 11 in the same direction at the time of CT imaging.

Radiation generated at the target layer is externally emitted through the target layer and the support substrate holding the target layer. The emission range of the radiation emitted from the emitter 10 is according to that restricted by an unshown forward shield, provided to the emitter 10. The irradiation region 13 is further defined by the collimator 12 provided between the emitter 10 and the accommodation portion 3.

The sensing device 11 is irradiated by the radiation. The collimator 12 restricts the irradiation region 13 so that the entire breast 15 of the subject P is irradiated, all the way to the tip, and so that the transmitted radiation forms a generally square shape on the sensing device 11. The irradiation region 13 is defined by the radiation transmitting portion formed in the collimator 12. When the entire breast 15 is within the irradiation region 13, the radiation which has been transmitted through the breast 15 reaches the sensing device 11, and thus a transmission image of within the breast 15 is obtained. Heavy metals which have radiation shielding properties, such as lead, tungsten, tantalum, rhenium, and so forth, are suitable as materials for the collimator 12.

The term "collimator 12" according to the present invention refers to a member formed of a radiation shielding material (hereinafter "shield material") which shields part of the radiation emitted from the emitter 10 of the radiation tube 8 so as to restrict part or all of the perimeter of the irradiation region 13. The collimator 12 can be configured of a frame of a shield material defining an opening serving as a radiation transmission portion (hereinafter "transmission portion"). Forming the collimator 12 so that the side of the frame facing the front face plate 7 has a cross-sectional shape in the form of the letter "U", or the equals symbol "=", so as to be opened forwards, facilitates attachment of the irradiation region 13 to the front face plate 7 side. A collimator 12 which is formed as a square frame surrounding the entire perimeter of the transmission portion serves to facilitate shielding of excessive radiation which might leak the front face plate 7 side. Also, the collimator 12 is provided separately from the radiation tube 8 and close to the accommodation portion 3, so the penumbra, which readily occurs in arrangements where the radiation tube 8 and collimator are integral and collimation is performed at a position away from the accommodation portion 3, can be reduced.

Shield

A plate-shaped shield 14 is provided on the inner side of the front face plate 7 of the gantry 2, surrounding the perimeter of the insertion opening 17, as illustrated in FIGS. 2A, 2B, and 3. The shield 14 is provided to isolate the irradiation region 13 and the subject P from each other, and follows the front face plate 7 between the rotation path of the collimator 12 and the rotation path of the emitter 10 created by rotation of the radiation tube 8. The shield 14 has an annular shape, with the middle portion corresponding to the insertion opening 17 and the accommodation portion 3 leading thereto being open. The shield 14 shields the subject P from direct irradiation by radiation from the emitter 10, scattered radiation occurring when radiation strikes the collimator 12, and so forth, thus preventing radiation from leaking to the subject P. Heavy metals which have high radiation shielding properties, such as lead, tungsten, tantalum, rhenium, and so forth, are suitable as materials for the shield 14. While the shield 14 is usually a circular annular shape, an elliptic annular shape, rectangular annular shape, or the like, may be employed. The shield 14 is disposed on the inner face of the front face plate 7, between the rotation path of the collimator 12 and the rotation path of the radiation tube 8.

The shield 14 has a gap 14c formed as to the insertion opening 17, and the collimator 12 is situated at a position corresponding to this gap 14c, as illustrated in FIG. 3. The front edge of the collimator 12 facing the front face plate 7 is situated closer to the front face plate 7 than the back face of the shield 14 in the Y direction, over the entire rotation path of the collimator 12. That is to say, the edge of the collimator 12 which faces the front face plate 7 is fit into the gap 14c. Thus, the front edge of the collimator 12 facing the front face plate 7 overlaps the thickness direction of the shield 14 when viewed from the Z direction. Accordingly, the collimator 12 can be brought into proximity with the front face plate 7 of the gantry 2, and the irradiation region 13 brought into proximity with the front face plate 7, so that CT imaging can be performed over a wide range, including the base of the breast 15. This arrangement where the front edge of the collimator 12 facing the front face plate 7 overlaps the shield 14 in the thickness direction thereof also contributes to suppressing leakage of radiation from between the collimator 12 and the shield 14.

The sensing device 11 may also be situated such that the edge is situated further toward the front face plate 7 than the back face of the shield 14 in the Y direction, on the rotation path of the collimator 12. The collimator 12 and sensing device 11 are both in close proximity to the accommodation portion 3, and are disposed facing each other.

While the edge of the collimator 12 facing the front face plate 7 is situated further toward the front face plate 7 than the back face of the shield 14 in the Y direction, over the entire rotation path of the collimator 12, this may be arranged to be part of the rotation path. For example, in a case where the collimator 12, radiation tube 8, and sensing device 11 have a rotation path for preliminary rotation other than the exposure period, the above-described arrangement does not necessarily have to be made for the preliminary rotation path.

Imaging System

Figure 4:
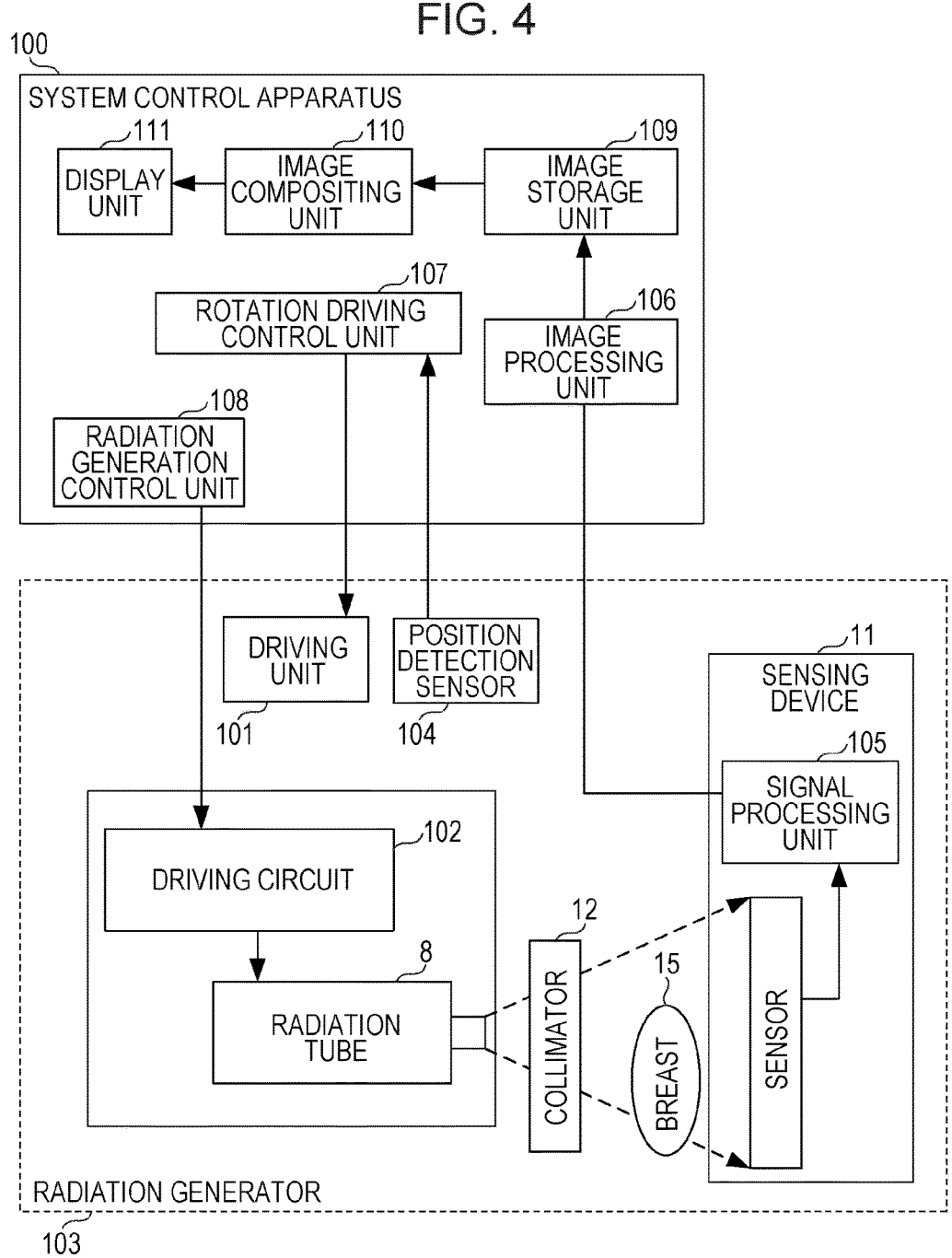
FIG. 4 is a configuration diagram of a mammographic CT apparatus system according to the present invention.

FIG. 4 is a configuration diagram illustrating the mammographic CT system according to the present invention. A system control apparatus 100 controls a radiation generator 103 including the radiation tube 8 and a driving circuit 102 thereof, the sensing device 11, and the driving unit 101. The driving circuit 102 outputs various types of control signals to the radiation tube 8 under control of a radiation generation control unit 108 of the system control apparatus 100. The rotation driving control circuit 107 outputs driving control signals to the driving unit 101, to perform driving of the aforementioned unshown rotating plate, so as to be rotated a predetermined amount, based on position information from a position detection sensor 104 and under control of the system control apparatus 100. The emission state of radiation emitted from the radiation generator 103 is controlled while rotating the driving unit 101 a pre-determined amount by the control signals. Radiation emitted from the radiation generator 103 is partially shielded by the collimator 12 and the like, passes through the breast 15, and is sensed at the sensing device 11. The sensing device 11 converts the sensed radiation into image signals, and outputs the image signals to a signal processing unit 105. The signal processing unit 105 subjects the image signals to pre-determined signals processing under control of the system control apparatus 100, and a CT image is generated by an image processing unit 106 within the system control apparatus 100, from the image information imaged at each rotation position, and stored in an image storage unit 109. The radiation tube 8 is rotated once around the accommodation portion 3 illustrated in FIGS. 2A and 2B, while multiple images are being taken. These images are composited at an image compositing unit 110, thereby generating a three-dimensional image, which is displayed on a screen of a display unit 111.

Second Embodiment

Figure 5A:
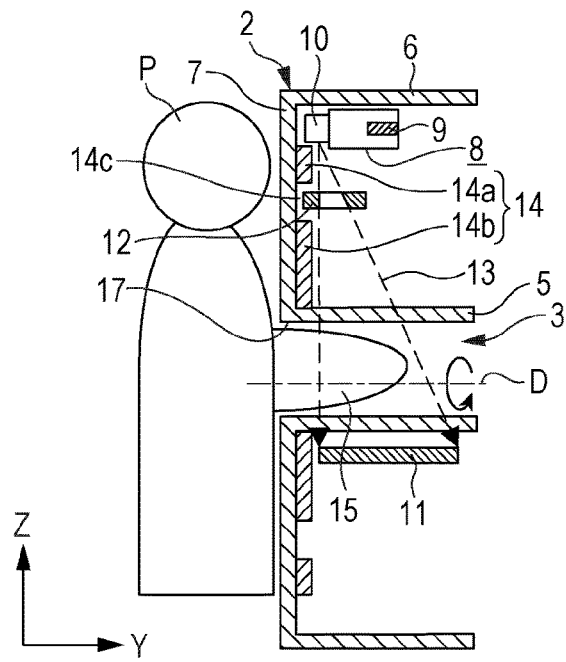
FIG. 5A is a cross-sectional view of a mammographic CT apparatus according to a second embodiment, as viewed from the X direction in FIG. 1.
Figure 5B:
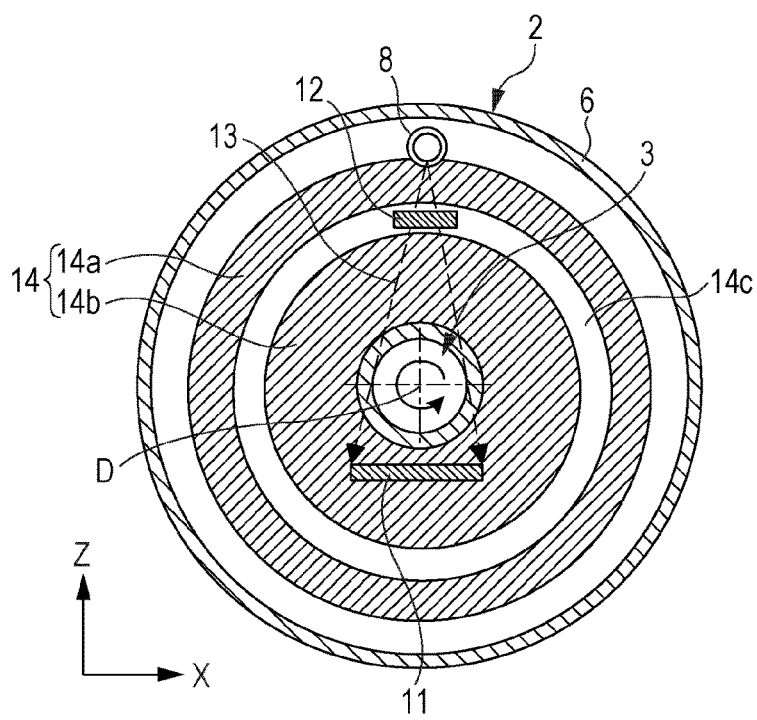
FIG. 5B is a cross-sectional view of the mammographic CT apparatus according to the second embodiment, as viewed from the Y direction in FIG. 1.

A second embodiment will be described. The shield 14, of which the center portion is opened, is disposed having been divided into an inner peripheral shield 14b on the insertion opening side and an outer peripheral shield 14a on the radiation tube side, as illustrated in FIGS. 5A and 5B. The gap 14c is formed between the inner peripheral shield 14b and the outer peripheral shield 14a. The collimator 12 is disposed at a position corresponding to the gap 14c, and the edge of the collimator 12 facing the front face plate 7 is situated closer to the front face plate 7 than the back face of the outer peripheral shield 14a in the Y direction. That is to say, the edge of the collimator 12 facing the front face plate 7 is fit into the gap 14c. Other configurations are the same as with the first embodiment described above.

This layout where the collimator 12 is situated on the radiation tube 8 side enables the size and weight of the collimator 12 to be reduced.

Third Embodiment

Figure 6A:
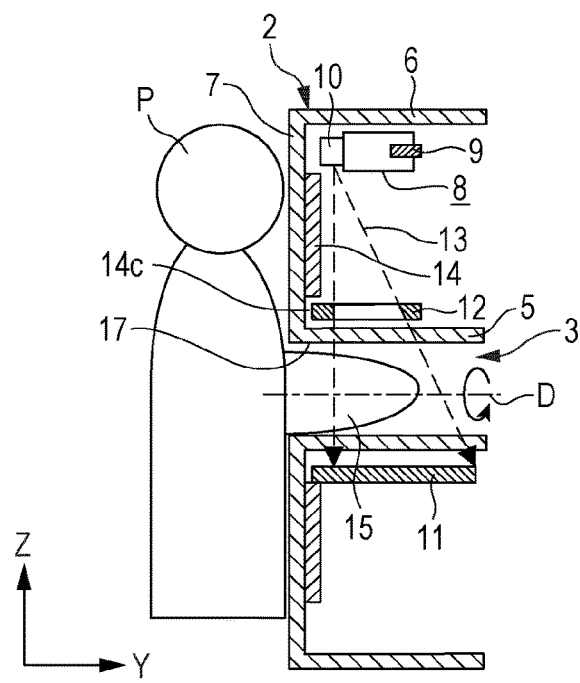
FIG. 6A is a cross-sectional view of a mammographic CT apparatus according to a third embodiment, as viewed from the X direction in FIG. 1.
Figure 6B:
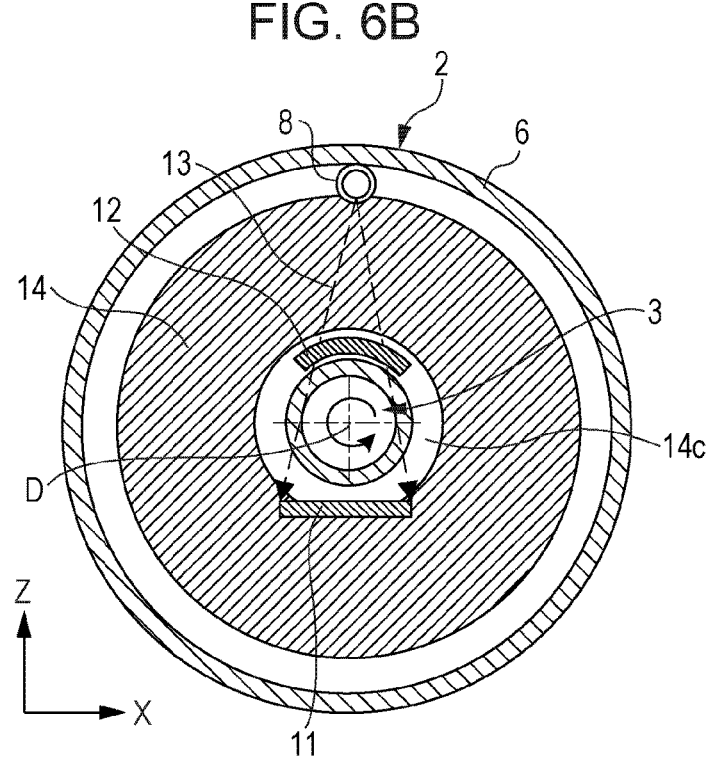
FIG. 6B is a cross-sectional view of the mammographic CT apparatus according to the third embodiment, as viewed from the Y direction in FIG. 1.
Figure 7:
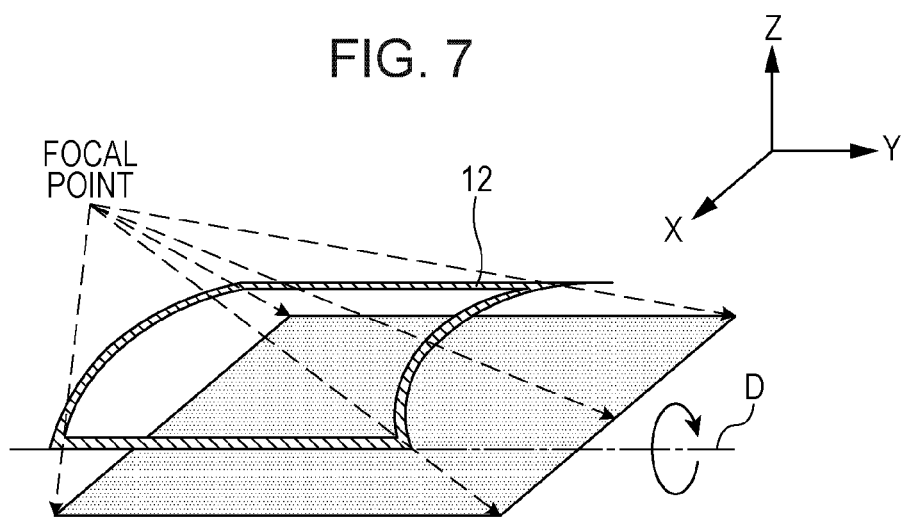
FIG. 7 is an enlarged perspective view of around a collimator according to the third embodiment.

A third embodiment will be described. The collimator 12 according to the third embodiment is curved three dimensionally, as illustrated in FIGS. 6A, 6B, and 7. Specifically, the collimator 12 is curved in a convex shape toward the outer side of rotation in the radial direction of rotation on the rotation axis D. Other configurations are the same as with the first embodiment described above.

Thus, reducing the width of the gap 14c between the insertion opening 17 and the shield 14 allows leakage of radiation from this region to be suppressed. The width of the gap 14c can be maximally reduced by matching the center of curvature of the collimator 12 with the rotation axis D.

Fourth Embodiment

Figure 8A:
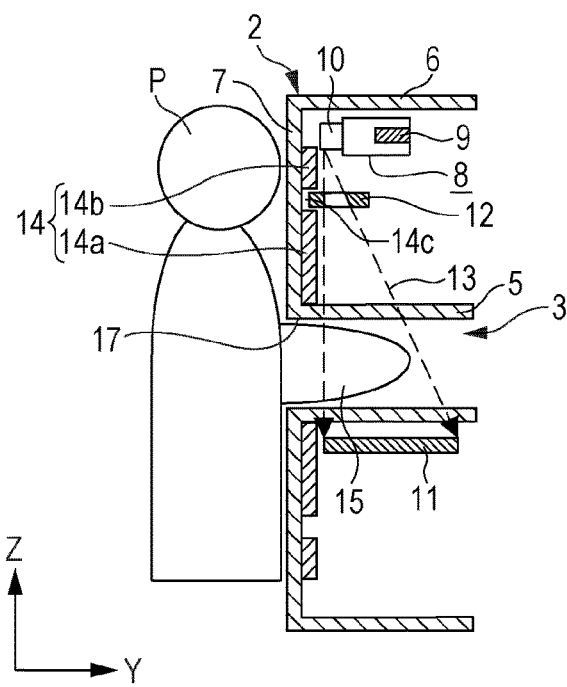
FIG. 8A is a cross-sectional view of a mammographic CT apparatus according to a fourth embodiment, as viewed from the X direction in FIG. 1.
Figure 8B:
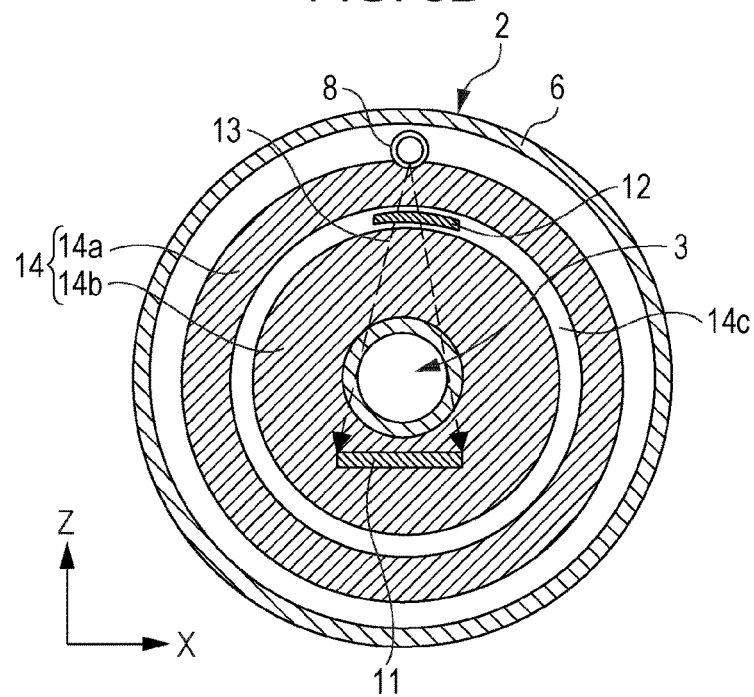
FIG. 8B is a cross-sectional view of the mammographic CT apparatus according to the fourth embodiment, as viewed from the Y direction in FIG. 1.

A fourth embodiment will be described. The fourth embodiment is the same as the second embodiment, other than the collimator 12 being curved as in the third embodiment, as illustrated in FIGS. 8A and 8B. Thus, the advantages of both the second and third embodiments can be had.

Fifth Embodiment

Figure 9A:
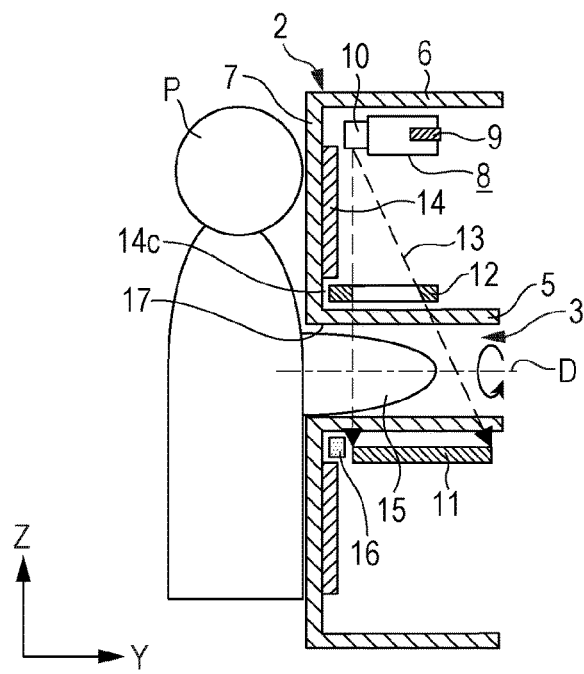
FIG. 9A is a cross-sectional view of a mammographic CT apparatus according to a fifth embodiment, as viewed from the X direction in FIG. 1.
Figure 9B:
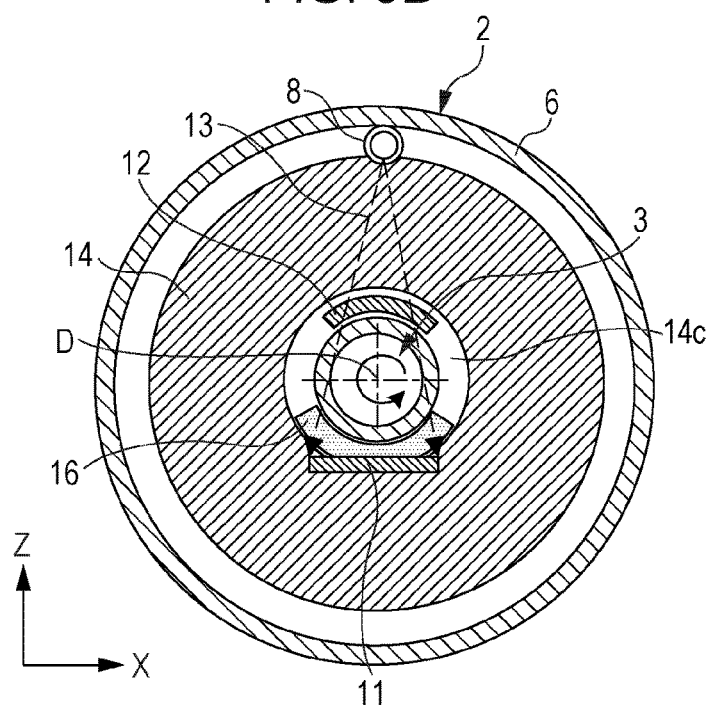
FIG. 9B is a cross-sectional view of the mammographic CT apparatus according to the fifth embodiment, as viewed from the Y direction in FIG. 1.

A fifth embodiment will be described. The shield 14 is provided with the gap 14c as to the insertion opening 17 in the same way as in the third embodiment, and a curved collimator 12 is disposed at a position corresponding to this gap 14c, as illustrated in FIGS. 9A and 9B. Further, the sensing device 11 is provided adjacent to the gap 14c, and a sub-shield 16 is provided which fills in at least the gap 14c where the sensing device 11 is adjacent. The sub-shield 16 rotates on the rotation axis D, synchronously with the sensing device 11 and in the same direction.

Providing the sub-shield 16 in this way can suppress scattered radiation occurring due to the sensing device 11 being irradiated by the radiation, from leaking from the gap 14c adjacent to the sensing device 11. The sub-shield 16 can be formed of the same material as the shield 14.

To maximize the above-described effect, the center of curvature of the collimator 12 preferably matches the rotation axis D, and the center of curvature of the sub-shield 16 also matches the rotation axis D. While the present embodiment is an embodiment where the sub-shield 16 has been applied to the third embodiment, the sub-shield 16 may be applied to other embodiments as well.

Sixth Embodiment

Figure 10A:
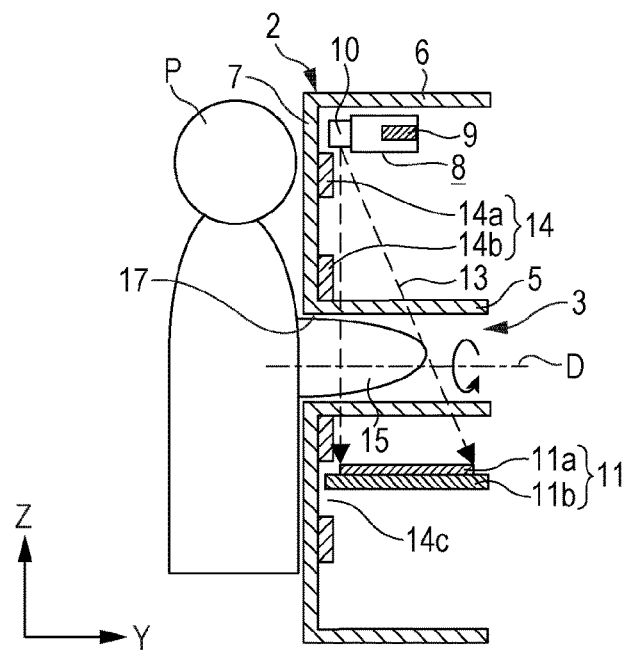
FIG. 10A is a cross-sectional view of a mammographic CT apparatus according to a sixth embodiment, as viewed from the X direction in FIG. 1.
Figure 10B:
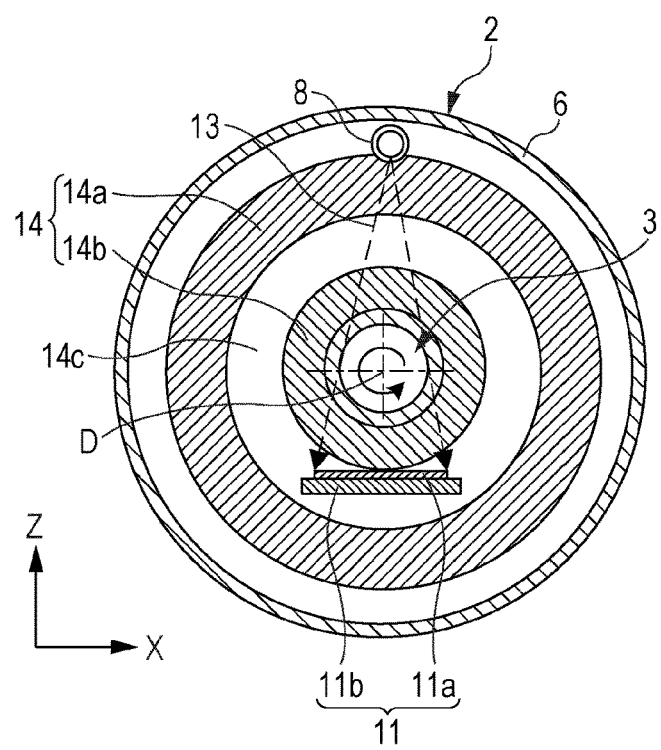
FIG. 10B is a cross-sectional view of the mammographic CT apparatus according to the sixth embodiment, as viewed from the Y direction in FIG. 1.
Figure 11:
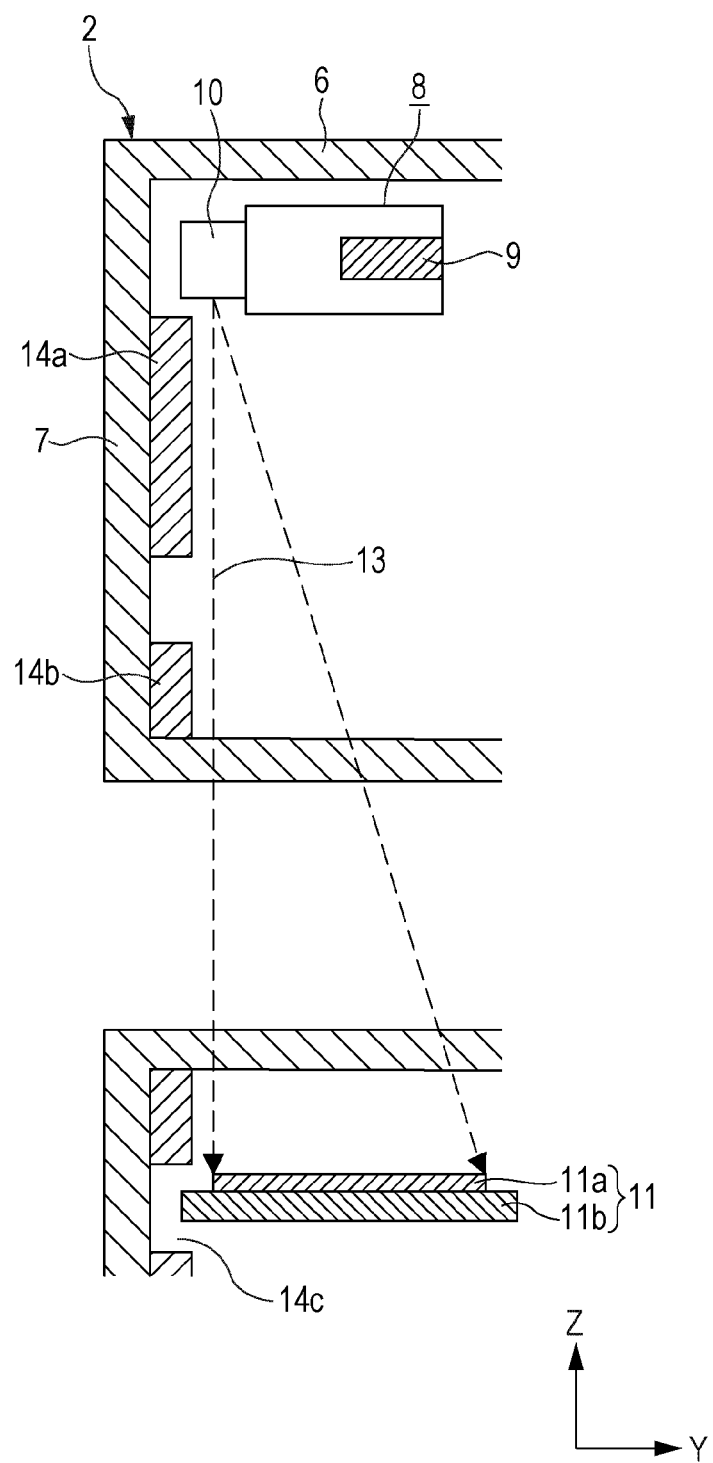
FIG. 11 is an enlarged view of around a collimator according to the sixth embodiment.

A sixth embodiment will be described. The radiation tube 8 is supported by the unshown rotating plate which is rotated by the driving unit 101 (see FIG. 4), and rotates on the rotational axis D extending in the direction of insertion and removal of the breast 15 to and from the accommodation portion 3, as illustrated in FIGS. 10A, 10B, and 11, by rotation of the rotating plate.

The sensing device 11 has a sensing area 11a at the middle portion thereof where radiation can be sensed, and a non-sensing area 11b at the perimeter portion where radiation cannot be sensed. The sensing device 11 according to the present embodiment has multiple sensing elements disposed in the sensing area 11a, and has signal lines connected to the multiple sensing elements disposed in the non-sensing area 11b. The sensing area 11a is of a size which matches that of the irradiation region 13 defined by the collimating functions of the emitter 10. The planar shape of the sensing area 11a is square. The sensing elements are not particularly restricted as long as they are elements capable of converting the intensity of incident radiation into electrical signals, but in the present embodiment are configured using photoelectric converting elements such as a complementary metal-oxide semiconductor (CMOS) sensor and fluorescent material. The sensing device 11 may be a digital sensor type sensing device having an A-D converter, from the perspective of compatibility with the imaging system.

A double-annular shield 14 is disposed on the inner side of the front face plate 7 of the gantry 2, surrounding the insertion opening 17. This shield 14 is divided into an inner peripheral shield 14b on the inner peripheral side (the perimeter of the insertion opening 17) and an outer peripheral shield 14a on the outer peripheral side (the perimeter of the outer peripheral plate 6), and a gap 14c is formed therebetween in an annular shape. The gap 14c is formed corresponding to the rotational movement path of the sensing device 11, with the sensing device 11 being provided at a position corresponding to the gap 14c, and the edge of the sensing device 11 facing the front face plate 7 is fit into the gap 14c. That is to say, the edge of the sensing device 11 facing the front face plate 7 is situated closer to the front face plate 7 than the back faces of the outer peripheral shield 14a and inner peripheral shield 14b in the Y direction. The edge of the sensing device 11 facing the front face plate 7 is fit into the gap 14c, and thus rotationally moves on the rotation axis D.

The shield 14 configured including the outer peripheral shield 14a and inner peripheral shield 14b shields the subject P from direct irradiation by radiation from the emitter 10, scattered radiation occurring when radiation strikes the sensing device 11, and so forth, thus preventing radiation from leaking to the subject P. Heavy metals which have high radiation shielding properties, such as lead, tungsten, tantalum, rhenium, and so forth, are suitable as materials for the shield 14. While the shield 14 (outer peripheral shield 14a and inner peripheral shield 14b) is usually a circular annular shape, an elliptic annular shape, rectangular annular shape, or the like, may be employed.

Thus, the front edge of the sensing device 11 facing the front face plate 7 overlaps the thickness direction of the shield 14 when viewed from the Z direction. Accordingly, the sensing device 11 can be brought into proximity with the front face plate 7 of the gantry 2 without being obstructed by the shield 14, and the sensing area 11a brought into proximity with the front face plate 7, so that CT imaging can be performed over a wide range, including the base of the breast 15. This arrangement where the front edge of the sensing device 11 facing the front face plate 7 overlaps the shield 14 in the thickness direction thereof when viewed from the Z direction also contributes to suppressing leakage of radiation from between the sensing device 11 and the shield 14.

Seventh Embodiment

Figure 12A:
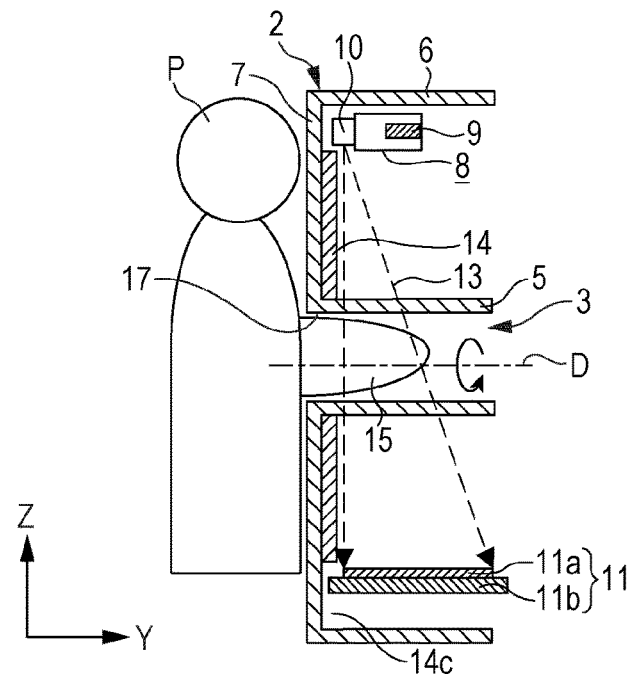
FIG. 12A is a cross-sectional view of a mammographic CT apparatus according to a seventh embodiment, as viewed from the X direction in FIG. 1.
Figure 12B:
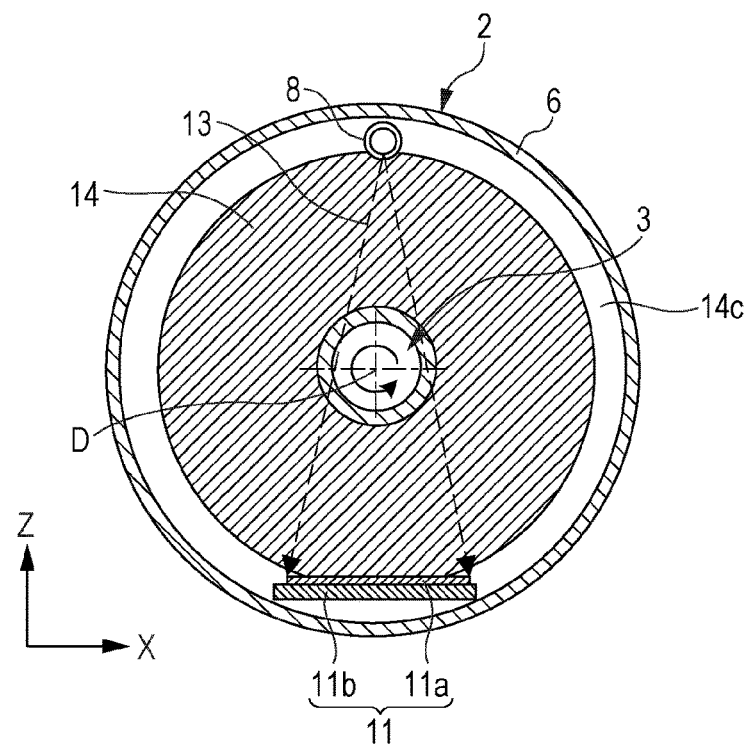
FIG. 12B is a cross-sectional view of the mammographic CT apparatus according to the seventh embodiment, as viewed from the Y direction in FIG. 1.

A seventh embodiment will be described. In the present embodiment, a single annular shield 14 is disposed on the inner face of the front face plate 7, with a gap 14c at the outer edge of the front face plate 7, as illustrated in FIGS. 12A and 12B. The sensing device 11 is provided at a position corresponding to the gap 14c, and the edge of the sensing device 11 facing the front face plate 7 is situated closer to the front face plate 7 than the back face of the shield 14 in the Y direction. Other configurations are the same as with the sixth embodiment described above.

Thus, this configuration where the irradiation region 13 essentially does not transverse the gap 14c enables more sure leakage prevention of radiation to the subject P than the sixth embodiment.

Eighth Embodiment

Figure 13A:
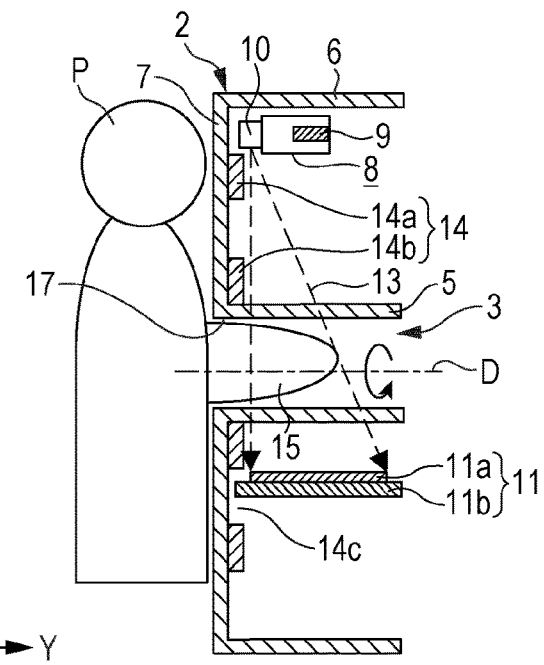
FIG. 13A is a cross-sectional view of a mammographic CT apparatus according to an eighth embodiment, as viewed from the X direction in FIG. 1.
Figure 13B:
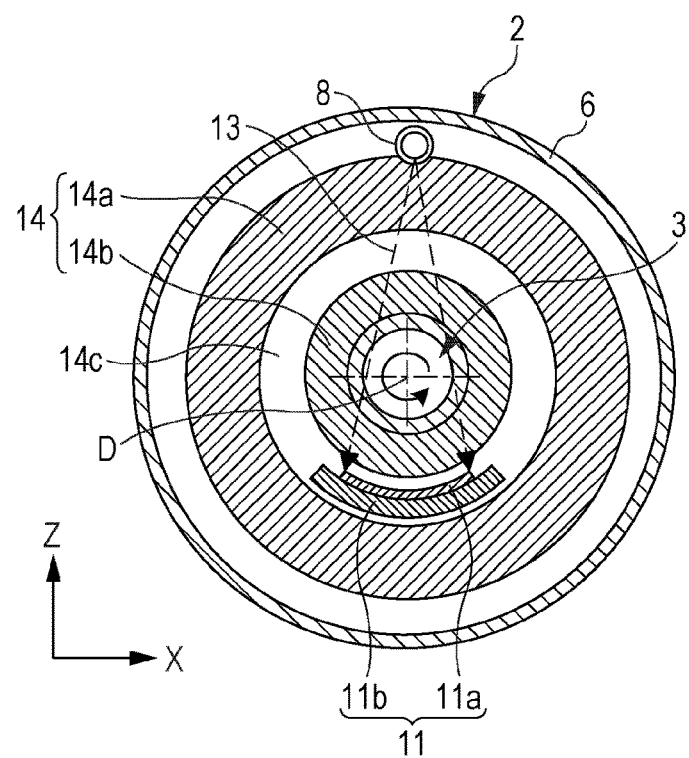
FIG. 13B is a cross-sectional view of the mammographic CT apparatus according to the eighth embodiment, as viewed from the Y direction in FIG. 1.

An eighth embodiment will be described. The sensing device 11 according to the eighth embodiment is curved three dimensionally, as illustrated in FIGS. 13A, and 13B. Specifically, the sensing device 11 is curved in a convex shape toward the outer side of rotation in the radial direction of rotation on the rotation axis D. Other configurations are the same as with the sixth embodiment described above.

This allows reduction of the width of the gap 14c between the outer peripheral shield 14a and inner peripheral shield 14b to be reduced, so leakage of radiation from this region can be suppressed. The width of the gap 14c can be maximally reduced by matching the center of curvature of the sensing device 11 with the rotation axis D.

Ninth Embodiment

Figure 14A:
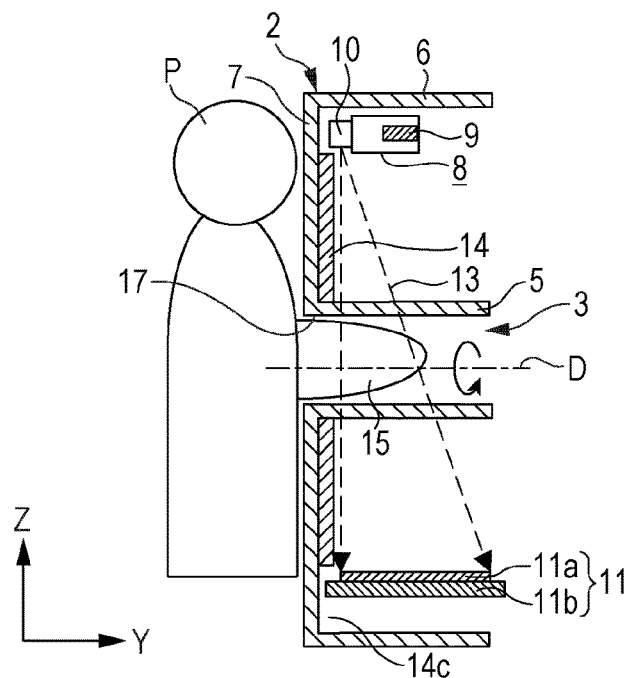
FIG. 14A is a cross-sectional view of a mammographic CT apparatus according to a ninth embodiment, as viewed from the X direction in FIG. 1.
Figure 14B:
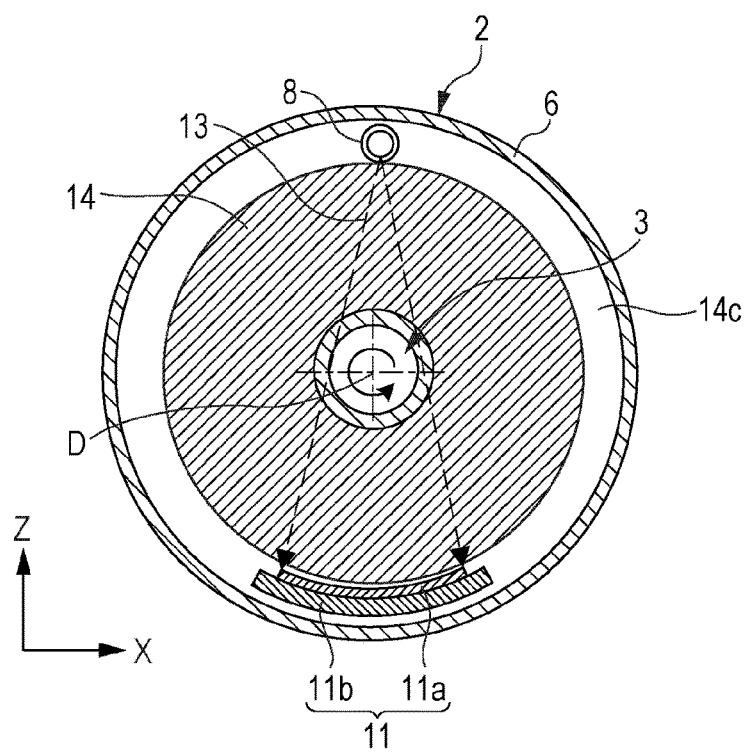
FIG. 14B is a cross-sectional view of the mammographic CT apparatus according to the ninth embodiment, as viewed from the Y direction in FIG. 1.

A ninth embodiment will be described. The present embodiment is the same as the seventh embodiment, other than the sensing device 11 being curved in a convex shape toward the outer side of rotation in the radial direction of rotation on the rotation axis D, as illustrated in FIGS. 14A and 14B. This allows reduction of the width of the gap 14c at the outer perimeter of the front face plate 7 to be reduced, so leakage of radiation from this region can be suppressed. The width of the gap 14c can be maximally reduced by matching the center of curvature of the sensing device 11 with the rotation axis D.

Tenth Embodiment

Figure 15A:
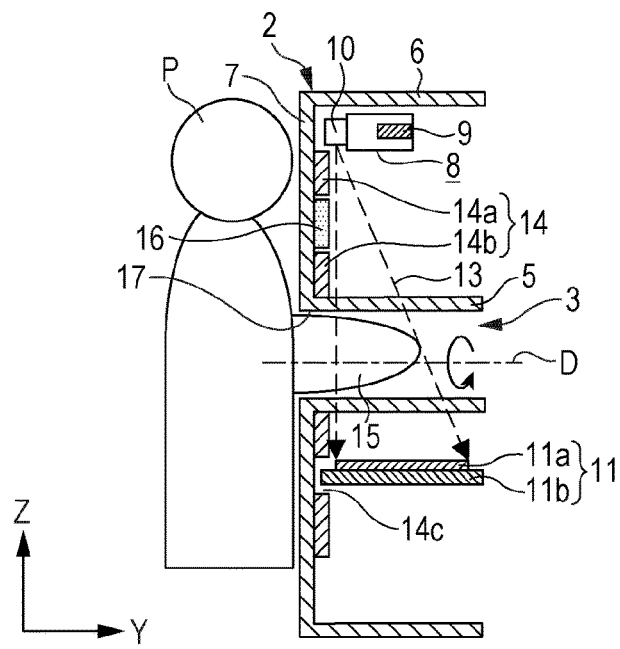
FIG. 15A is a cross-sectional view of a mammographic CT apparatus according to a tenth embodiment, as viewed from the X direction in FIG. 1.
Figure 15B:
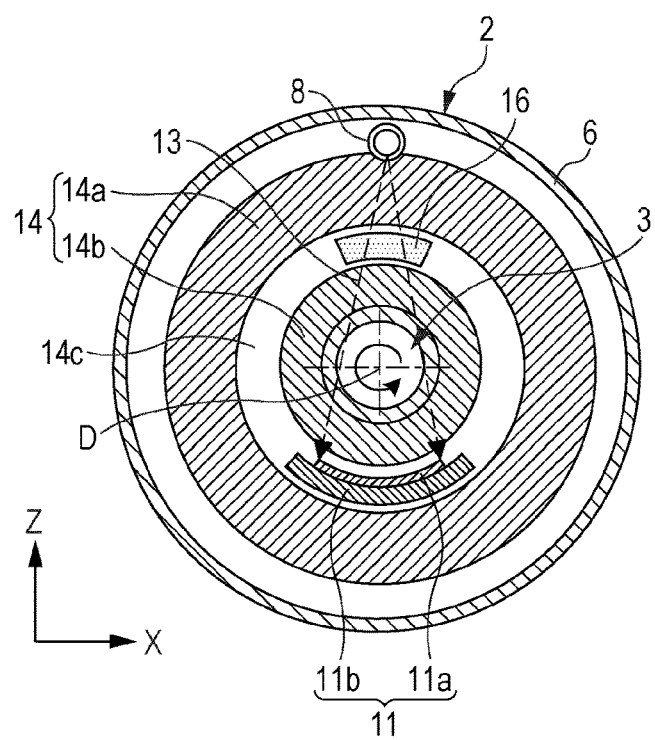
FIG. 15B is a cross-sectional view of the mammographic CT apparatus according to the tenth embodiment, as viewed from the Y direction in FIG. 1.

A tenth embodiment will be described. The present embodiment is the same as the sixth embodiment, other than being provided with the sub-shield 16 which fills in the gap 14c in the region overlapped by the irradiation region 13 from the emitter 10 to the accommodation portion 3, which rotates on the rotation axis D synchronously with the sensing device 11 in the same direction, as illustrated in FIGS. 15A and 15B.

Thus, leakage of radiation from the gap 14c situated between the emitter 10 and accommodation portion 3 can be suppressed. The sub-shield 16 is effective when provided in the gap 14c in the irradiation region 13 from the emitter 10 to the accommodation portion 3, and can improve radiation leakage preventing effects by being provided over an even wider region.

According to the present invention, providing the collimator near to the accommodation portion enables the penumbra of radiation which spreads outwards from the irradiation region to be suppressed. Also, an annular shield is provided between the rotational path of the collimator and the rotational path of the radiation tube, so leakage of scattered radiation due to the collimator to the subject can be prevented. Also, providing the collimator near to the front face plate enables radiation imaging to the base of the breast.

Further, providing the sensing device near to the front face plate enables radiation imaging to the base of the breast to be performed more effectively.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application Nos. 2013-239624 and 2013-239625, filed Nov. 20, 2013, which are hereby incorporated by reference herein in their entirety.

REFERENCE SIGNS LIST

1 Mammographic CT apparatus
2 Gantry
3 Accommodation portion
7 Front face plate
8 Radiation tube
11 Sensing device
12 Collimator
14 Shield
14c Gap
15 Breast
101 Driving unit
P Subject
D Rotation axis

The invention claimed is:

1. A mammographic CT apparatus comprising:
   a gantry, including a front face plate in which an insertion opening is formed for inserting a breast into an accommodation portion;
   a radiation tube disposed within the gantry;
   a sensing device disposed within the gantry so as to face the radiation tube, and configured to sense radiation which has been emitted from the radiation tube and been transmitted through the accommodation portion;
   a driving unit configured to rotate the radiation tube and the sensing device around a rotation axis set in the normal direction of the accommodation portion, at the same angular speed and in the same direction;
   a collimator disposed between the accommodation portion and the radiation tube, and configured to rotate around the rotation axis integrally with the radiation tube and sensing device; and
   an annular shield disposed between the rotational path of the collimator and the rotational path of the radiation tube, having an annular gap corresponding to the rotational path of the collimator,
   wherein an edge of the collimator is fit into the gap.

2. The mammographic CT apparatus according to claim 1, wherein the edge of the collimator is fit into the gap over the entire rotational path.

3. The mammographic CT apparatus according to claim 1, wherein an edge of the sensing device is fit into the gap.

4. The mammographic CT apparatus according to claim 1, further comprising:
   a sub-shield;
   wherein the sensing device is disposed at a position in the gap, and the sub-shield fills in the gap at the portion where the edge of the sensing device is, and rotates around the rotation axis synchronously with the sensing device and in the same direction.

5. The mammographic CT apparatus according to claim 1, wherein the shield includes an inner peripheral shield provided to the side of the insertion opening and an outer peripheral shield provided to the side of the radiation tube, the gap being formed between the inner peripheral shield and the outer peripheral shield.

6. The mammographic CT apparatus according to claim 5, further comprising:
   a sub-shield which fills in the gap at a position overlapped by an irradiation region which extends from an emitter of the radiation tube to the accommodation portion, and rotates around the rotation axis synchronously with the sensing device and in the same direction.

7. A mammographic CT apparatus comprising:
   a gantry, including a front face plate in which an insertion opening is formed for inserting a breast into an accommodation portion;
   a radiation tube disposed within the gantry;
   a sensing device disposed within the gantry so as to face the radiation tube, and configured to sense radiation which has been emitted from the radiation tube and been transmitted through the accommodation portion;
   a driving unit configured to rotate the radiation tube and the sensing device around a rotation axis set in the normal direction of the accommodation portion, at the same angular speed and in the same direction; and
   an annular shield which surrounds the perimeter of the insertion opening, disposed on an inner side of the front face plate, and having an annular gap corresponding to the rotational path of the sensing device,
   wherein an edge of the sensing device is fit into the gap.

8. A computed tomography apparatus for breast comprising:
   a gantry, including a front face plate in which an insertion opening is formed for inserting a breast into an accommodation portion;
   a radiation tube disposed within the gantry;
   a sensing device disposed within the gantry so as to face the radiation tube, and configured to sense radiation which has been emitted from the radiation tube and been transmitted through the accommodation portion;
   a driving unit configured to rotate the radiation tube and the sensing device around a rotation axis integrally;
   a collimator disposed between the accommodation portion and the radiation tube, and configured to rotate around the rotation axis integrally with the radiation tube and sensing device; and
   an annular shield disposed between the rotational path of the collimator and the rotational path of the radiation tube, having an annular gap corresponding to the rotational path of the collimator,
   wherein an edge of the collimator is located in the gap.

9. The computed tomography apparatus according to claim 8, wherein the edge of the collimator is located in the gap over the entire rotational path.

10. The computed tomography apparatus according to claim 8, wherein an edge of the sensing device is located in the gap.

11. The computed tomography apparatus for breast according to claim 8, further comprising:
    a sub-shield located in the gap for the collimator in opposition to the collimator with respect to the rotation axis;
    wherein the sub-shield is configured to be rotated around the rotation axis synchronously with the sensing device and in the same direction.

12. The computed tomography apparatus according to claim 8, wherein the collimator is curved in a convex shape toward the outer side of rotation in a radial direction of rotation on the rotation axis.

13. The computed tomography apparatus according to claim 12, wherein the center of curvature of the collimator matches the rotation axis.

14. The computed tomography apparatus according to claim 8, wherein the shield includes an inner peripheral shield provided to the side of the insertion opening and an outer peripheral shield provided to the side of the radiation tube, the gap being formed between the inner peripheral shield and the outer peripheral shield.

15. The computed tomography apparatus according to claim 14, further comprising:
    a sub-shield located in the gap at a position overlapped by an irradiation region which extends from an emitter of the radiation tube to the accommodation portion, and rotates around the rotation axis synchronously with the sensing device and in the same direction.

16. The computed tomography apparatus according to claim 8, wherein the edge of the collimator is overlapped with the annular shield in viewing from along a radial direction of the gantry.

17. A computed tomography apparatus comprising:
    a gantry, including a front face plate in which an insertion opening is formed for inserting a breast into an accommodation portion;
    a radiation tube disposed within the gantry;
    a sensing device disposed within the gantry so as to face the radiation tube, and configured to sense radiation which has been emitted from the radiation tube and been transmitted through the accommodation portion;

a driving unit configured to rotate the radiation tube and the sensing device around a rotation axis integrally; and an annular shield which surrounds the perimeter of the insertion opening, disposed on an inner side of the front face plate, and having an annular gap corresponding to the rotational path of the sensing device, wherein an edge of the sensing device is located in the gap.

18. The computed tomography apparatus according to claim 17, wherein the sensing device has a sensing area at the middle portion thereof where radiation can be sensed, and a non-sensing area at the perimeter where radiation cannot be sensed, and wherein the edge of the sensing device which is located in the gap is a non-sensing area.

19. The computed tomography apparatus according to claim 17, wherein the gap is formed between outer perimeter of the shield and an outer peripheral plate of the gantry.

20. The computed tomography apparatus according to claim 17, wherein the sensing device is curved in a convex shape toward the outer side of rotation in the radial direction of rotation on the rotation axis.

21. The computed tomography apparatus according to claim 20, wherein the center of curvature of the sensing device matches the rotation axis.

22. The computed tomography apparatus according to claim 17, wherein the edge of the sensing device is overlapped with the annular shield in viewing from along a radial direction of the gantry.

* * * * *